(12) United States Patent
Cordaro (10) Patent No.: US 7,771,474 B2
(45) Date of Patent: Aug. 10, 2010

(54) TRANSVERSE CONNECTOR SYSTEM

(75) Inventor: Nicholas M. Cordaro, Oceanside, CA (US)

(73) Assignee: SeaSpine, Inc., Vista, CA (US)

(*) Notice: Subject to any disclaimer, the term of this patent is extended or adjusted under 35 U.S.C. 154(b) by 605 days.

(21) Appl. No.: 11/492,154

(22) Filed: Jul. 24, 2006

(65) Prior Publication Data

US 2006/0259038 A1    Nov. 16, 2006

Related U.S. Application Data

(63) Continuation-in-part of application No. 10/877,667, filed on Jun. 24, 2004, now Pat. No. 7,160,301.

(60) Provisional application No. 60/483,947, filed on Jul. 1, 2003.

(51) Int. Cl.
*A61B 17/70* (2006.01)
*A61B 17/88* (2006.01)

(52) U.S. Cl. ............ 623/17.11; 606/250; 606/251; 606/252; 606/253; 606/257; 606/260; 606/264; 606/270; 606/276; 606/277; 606/278; 606/279

(58) Field of Classification Search ......... 606/250–253, 606/257, 260, 270, 276–279
See application file for complete search history.

(56) References Cited

U.S. PATENT DOCUMENTS

| | | | | |
|---|---|---|---|---|
| 5,549,607 A | * | 8/1996 | Olson et al. | 606/251 |
| 5,947,966 A | * | 9/1999 | Drewry et al. | 606/252 |
| 6,283,967 B1 | * | 9/2001 | Troxell et al. | 606/252 |
| 6,872,208 B1 | * | 3/2005 | McBride et al. | 606/86 A |
| 2004/0116928 A1 | * | 6/2004 | Young et al. | 606/61 |
| 2005/0228377 A1 | * | 10/2005 | Chao et al. | 606/61 |
| 2006/0100626 A1 | * | 5/2006 | Rathbun et al. | 606/69 |
| 2006/0206114 A1 | * | 9/2006 | Ensign et al. | 606/61 |

* cited by examiner

*Primary Examiner*—Thomas C Barrett
*Assistant Examiner*—Sameh Boles (57) ABSTRACT

A transverse connector system for interconnecting two spinal rods includes a connector arranged to span the distance between the rods with a rod receiving recess and a pin receiving bore on each end. A one-piece pin member such as a set screw is disposed within each bore with an enlarged head protruding from the bottom of the connector so that when the set screw is retracted into the bore the head engages a side of the respective rod to clamp the rod within the recess. The connector may comprise two elongated members with a recess and pin receiving bore at one end of each member, a middle coupler which allows three degrees of freedom between the members to accommodate any anticipated spatial orientation between the members and a set screw for securing the other ends of the members together.

14 Claims, 10 Drawing Sheets

TRANSVERSE CONNECTOR SYSTEM

RELATED APPLICATION

This application is a continuation-in-part of U.S. application Ser. No. 10/877,667 filed Jun. 24, 2004 which issued as U.S. Pat. No. 7,160.301, entitled Transverse Connector System which claims priority of U.S. Provisional Application Ser. No. 60/483,947, filed Jul. 1, 2003, entitled Variable Transverse Connector.

FIELD OF THE INVENTION

The present invention relates to a transverse connector system for interconnecting spinal rods that retain vertebrae in a fixed position. Another aspect of the invention is directed to a transverse connector system which is readily adjustable to join spinal rods of differing spatial orientations.

DESCRIPTION OF THE PRIOR ART

Numerous techniques have been employed to rigidly connect a pair of spinal rods for facilitating spinal fusion. A transverse connector system including one or more longitudinal members adapted to span the distance between two spinal rods along with a means for securing the end or ends of longitudinal member(s) to the spinal rods is generally used.

For example, see U.S. Pat. No. 5,522,816 ("'816 patent") issued to Dinello et al which discloses an elongated plate extending between a pair of hooks which are clamped to the respective rods by set screws. The set screws are positioned at a right angle to and extendable from the top surface of the respective hook with a portion of the hook extending completely underneath the spinal rod. This concept is disadvantageous in the clinical setting because bone or soft tissue protruding up to the lower surface of the spinal rod may restrict the ability of the surgeon in placing the lower hook portion underneath the spinal rod. U.S. Pat. No. 5,624,442 ("'442 patent") to Mellinger et al discloses a transverse connector rod clamping hook arrangement similar to the '816 hook configuration in that a portion of the hook is designed to extend under the rod.

U.S. Pat. No. 6,113,600, issued to Drummond et al, discloses a transverse connector which, to an extent, overcomes the problem associated with the '816 patent by positioning the set screws at an oblique angle relative to the longitudinal axis of the connector. This allowed for less of the rod engaging portion to extend underneath and around the spinal rod, slightly increasing the clinical usability. However, a clinical disadvantage of the '600 device is that the tightening mechanism is designed to extended parallel to the set screw, at the same oblique angle. A deep and narrow surgical wound site greatly limits the angle at which an instrument may protrude resulting in the probability that increased soft tissue retraction and/or dissection may be required.

U.S. Pat. No. 6,413,258, issued to Bernhardt Jr. ("Bernhardt") discloses a transverse coupler in which a two-piece screw/flanged nut assembly is employed to force a spinal rod within a concavity in each end of the coupler. This two part spinal rod clamping arrangement is disadvantageous for several reasons including the costs of making the separate parts, the likelihood that one of the screw or nuts will become lost or misplaced during the assembly and/or installation process and the cost of machining the lower end of the through bore in the coupler to accommodate the rectangular flats of the nuts to prevent rotation thereof.

The current invention provides the advantages of functioning properly with bone or soft tissue extending completely up to the bottom surface of the spinal rod and accommodating simple instrumentation that extends directly out of the wound site without additional soft tissue retraction or dissection.

With respect to transverse connector systems designed to accommodate differing spatial orientations of the spinal rods see U.S. Pat. No. 5,980,523 (Jackson); U.S. Pat. No. 6,217,578 (Crozet et al); and U.S. Pat. No. 6,544,832 (Shulzas). All three patents disclose transverse connector systems including elongated members extending between the rods that allow for three degrees of freedom between the members, i.e., translational, rotational and pivotal movement.

To accommodate the three degrees of freedom, the Jackson connector system requires a hooked end element secured to each rod via a set screw, a separate linking element positioned between the end elements and two screws to secure the separate linking element to the hooked end elements. This arrangement requires, not only the additional linking element, but requires the surgeon to tighten four screws to secure the rods in the desired position.

The Crozet et al cross connector system employs a pivot element positioned between hook elements anchored to the spinal rods via set screws with the pivot element being secured to one end of one of the hook elements by means of a threaded shaft and a hex nut. This arrangement requires the use of two separate tools (one for the set screws and one for the nut) to secure the rods in the desired orientation. In addition, the nut tightening tool may disturb the tissue surrounding the nut during the tightening procedure at best or at worst may be deflected by the nut into adjacent vertebrae in the event that the tool slips off of the nut.

Blackstone Medical Inc., of Springfield, Mass., has introduced a transverse connector system capable of accommodating common spatial orientation of spinal rods in which an external hex nut, rounded along the top edges, apparently to reduce tissue abrasion, is used to lock the connector elements together. This type of nut has the same disadvantages as the Crozet et al nut.

The Shulzas transverse connector system employs two elongated members with each member clamped at the first end to a respective rod. The second end of one of the members is in the form of a shaft which extends through a ball joint positioned in a truncated opening in the second end of the other member. The member having the truncated opening not only necessarily has a considerable width, but would be relatively expensive to manufacture. It is to be noted that Jackson, Crozet et al and Shulzas connectors all suffer from the use of rod clamping set screws which are oriented at an oblique angle to the longitudinal axis of the connector.

There is a need for a transverse connector system which overcomes the above disadvantages.

SUMMARY OF THE INVENTION

A transverse connector system for interconnecting two spinal rods, in accordance with the present invention, includes a connector, formed of one or more elongated members, adapted to span the distance between the rods. The connector has a rod receiving recess or groove on each end and a pin receiving bore adjacent each recess. A one part pin member, such as a clamping set screw, is positioned within each pin receiving bore with the pins being arranged to be retracted within their associated bores to clamp the rods within the recesses and rigidly join the rods to the connector. Preferably the pins are set screws with enlarged heads having beveled sides extending below the pin receiving bores so that the beveled sides, which may be straight or concave, engage the side of the rods to clamp the rods within the respective recesses.

To simplify the installation procedure the clamping set screws and pin receiving bores are preferably reverse threaded to accommodate clockwise rotation of the screws for the tightening procedure. Means are preferably provided to ensure that the clamping set screw, once installed in the respective pin receiving bore at the factory, cannot exit the bore while allowing sufficient movement along the bore axis accommodating the receipt and locking of the rod within the recess. For example, the clamping set screw may be formed with an interrupted threaded portion having an intermediate section with a diameter less than the root diameter of the threaded portion. A stop member in the form of a dowel pin intersects the pin receiving bore within the thread depth and in the area occupied by the intermediate section of the set screw. The stop member is arranged to engage a lower branch of the bifurcated thread to prevent the set screw from exiting the connector. In addition, the rod receiving recesses in the connector may be formed with an arc exceeding 180° and have a slightly smaller radius than the rod to allow the arc to slightly deform when the rod is forced therein to provide a clamping action between the rod and the connector end defining the recess.

To facilitate the installation of the system while accommodating a reasonable spatial orientation of the spinal rods, the connector may be formed of first and second elongated members, a middle coupler and a coupler locking screw. Each elongated member defines a longitudinal axis, a rod receiving groove on a proximal end thereof and a pin receiving bore adjacent the groove. A clamping pin is disposed in each pin receiving bore for securing the proximal ends of the members to a respective rod. The distal end of the first member is provided with a threaded locking screw receiving bore. A ring coupler is mounted over the distal end of the first member for limited pivotal movement about an axis perpendicular to the longitudinal axis of that member. The coupler has an upper section with a cylindrical opening therein positioned over the locking screw receiving opening and a lower section of the coupler defines an internal curved surface through which the distal end of the second member extends to allow the second member to move along and rotate about it's longitudinal axis relative to the first member. A coupler locking screw, threaded into the locking screw receiving bore in the coupler, is arranged, when tightened, to lock the distal ends of the first and second members together to maintain the spinal rods in the desired spatial orientation. Preferably means are provided to retain the coupler set screw within the coupler and the locking screw receiving bore after assembly at the factory while allowing the set screw limited movement along the axis of the locking screw receiving bore to secure the elongated members together.

The present invention, as to its construction and function, may best be understood by reference to the accompanying description taken in conjunction with the appended drawings.

DESCRIPTION OF THE PREFERRED EMBODIMENT

Figure 1:
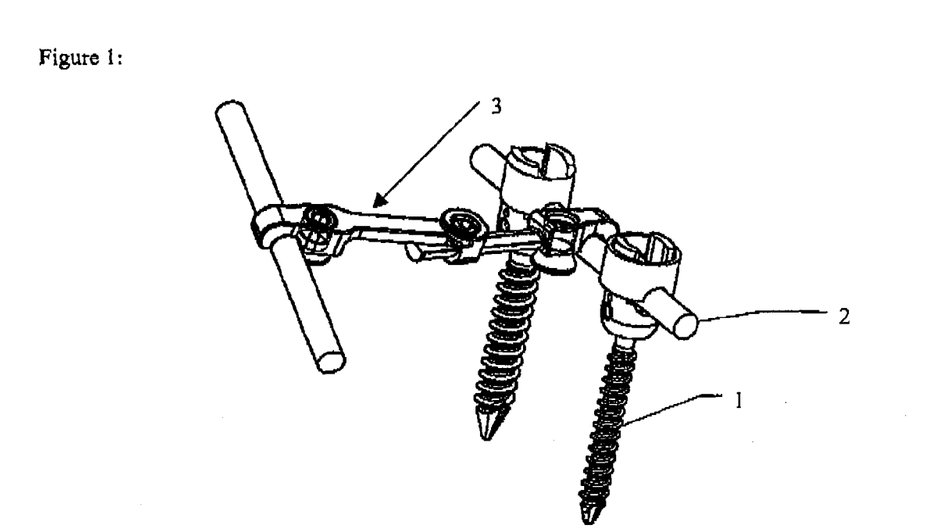
FIG. 1 is a side elevation view of a transverse connector system in accordance with the present invention wherein the connector is formed of a single unitary element.
Figure 2:
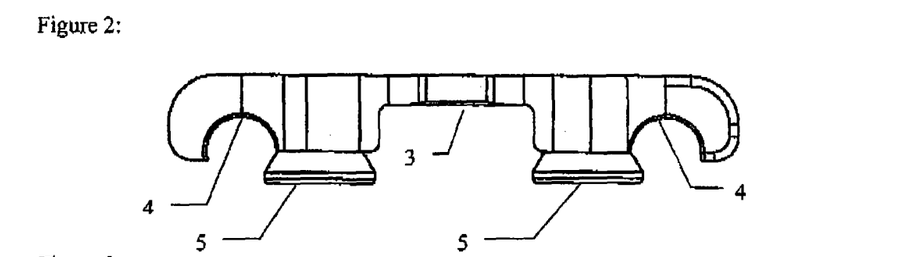
FIG. 2 is a top plan view of the connector system of FIG. 1.

Referring now to FIGS. 1 and 2 an elongated unitary connector 10 is arranged to span the distance between two spinal rods. The connector is formed with end sections 12 defining rod receiving surfaces, grooves or recesses 14 and an intermediate bridge section 16. A threaded clamping pin, e.g., set screw, receiving bore 18 is located adjacent each groove 14 and extends at a right angle to the top surface 19 and the longitudinal axis $X_1$ of the member 10 as illustrated. This arrangement overcomes the problems associated with prior art spinal rod securing systems which require the use of tightening instrumentation oriented at an angle to the wound site. A pin 20, in the form of a clamping set screw with an internal hexagonal wrench receiving surface 22, e.g., to accommodate an alien wrench, and an enlarged head 24 is threaded into each bore 18 from the bottom to complete the system.

The rod receiving grooves 14 are generally semi-cylindrical in shape with a radius which may be slightly greater than or smaller than the radius of the spinal rod 26 to be clamped within the groove. See FIG. 4. The enlarged head 24 of each set locking member such as clamping screw 20 has an outwardly and downwardly inclined or beveled surface 24a which may be formed as a straight, i.e., conical, surface as is illustrated in FIGS. 1 and 4 or with a concave surface on the lower end thereof having a radius the same or slightly greater than the radius of the rod as is shown in FIG. 5.

Figure 3:
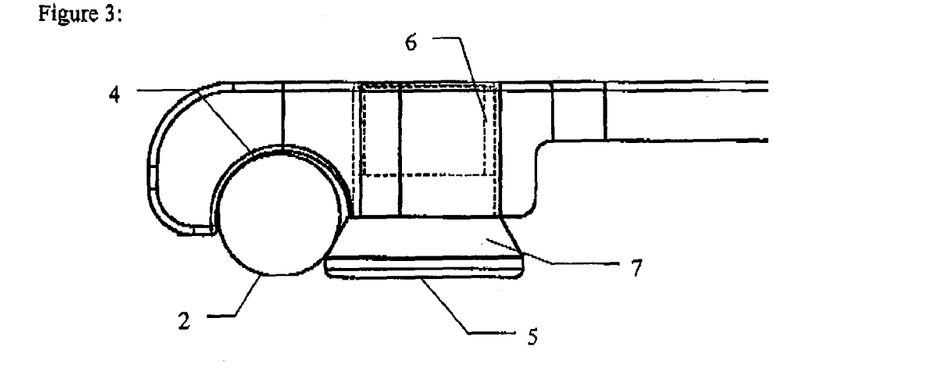
FIG. 3 is a side elevation view of a modified connector system in which one of the rod receiving grooves is located remote from the center section.

It is to be noted that one or both of the rod grooves may be located on the exterior side of the elongated members, i.e., remote from the bridge section 16, indicated at 14' in FIG. 3.

Figure 4:
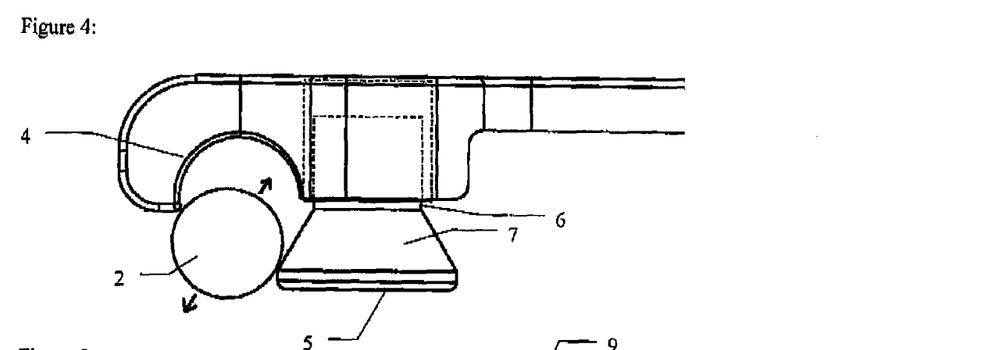
FIGS. 4 and 5 are side elevation views, partially broken away, of the assembly of FIG. 2 showing the path of the spinal rod into and captured within the rod receiving groove in the connector.

Prior to placement of the connector in the patient, the set screws 20 are in their lowered position, as is illustrated in FIGS. 1 and 4, leaving ample room for the placement of the connector ends over the rods. The clearance $d_1$ between the terminal end 14a of the groove and the side 24a of the set screw 20, in its lowered position, is greater than the diameter of the spinal rod. This allows the connector end with its rod receiving groove to be inserted over or removed from the rod as is illustrated in FIG. 4.

Figure 5:
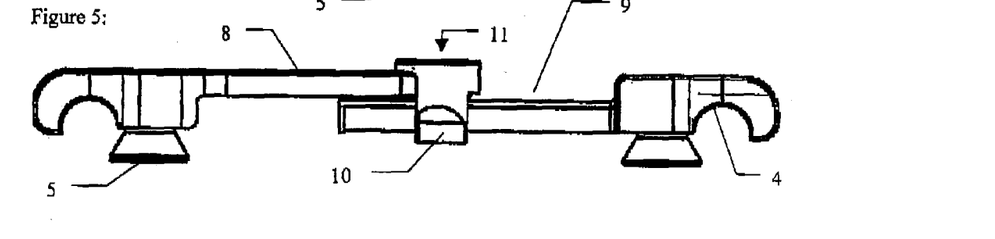
Figure 6:
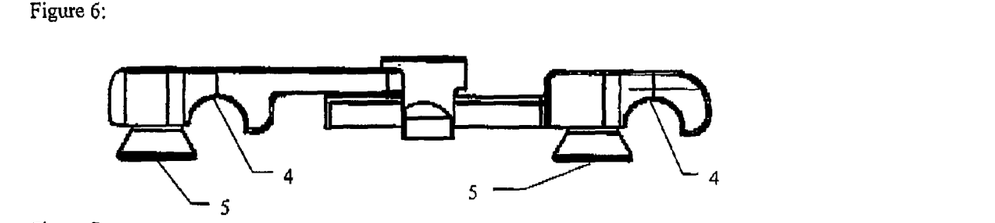
FIG. 6 is a perspective view of a universal transverse connector system in which the connector is formed of two members with one end of each member secured to a respective spinal rod via two pedical screws.

If the rod is positioned at least part way into the groove, the clamping set screw 20 may be retracted to force the connector end down to clamp the rod within the groove as is illustrated in FIG. 5. If the rod is fully seated within the groove the set screw may be retracted to complete the clamping action. With the set screw retracted the arc extending from the terminal end 14a of the groove to the side of the set screw 20 which contacts the side of the rod exceeds 180°.

During installation the surgeon will probably be required to bend and/or twist the bridge section 16 to provide the proper orientation between the connected spinal rods. It is to be noted that the connector may be formed of two or more elements which can be moved longitudinally, rotated and/or pivoted relative to each other to eliminate the necessity for the surgeon to bend and/or twist a portion of the connector to accommodate the desired spatial orientation of the rods.

A preferred universal or variable connector is illustrated in FIGS. 6-13 in which the connector includes first and second elongated members designated 28 and 48, respectively, connected between spinal rods 26. Pedical screws 32 (for insertion into the selected vertebrae not shown) are secured to one of the spinal rods for illustrative purposes. The elongated members 28 and 48 define longitudinal axis $X_2$ and $X_3$ respectively. Each member has a rod receiving groove 14 at a proximal end 28a or 48a thereof and a threaded pin/set screw receiving bore 18 adjacent thereto. As described with respect to FIGS. 2 and 3, the bores 18 are oriented at 90° with respect to the respective longitudinal axis and the top surfaces of the proximal ends as shown. It is to be noted that while the retractable clamping screw arrangement of FIGS. 1 and 2 is preferred as the means to secure the spinal rods in the embodiment of FIGS. 6-13, a more conventional clamping system, such as those disclosed in the prior art, could be used for this variable connector system.

Figure 7:
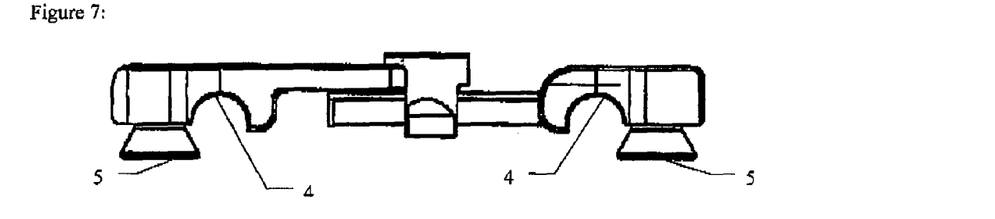
FIG. 7 is a side elevation view of the disassembled connector system of FIG. 6.
Figure 8:
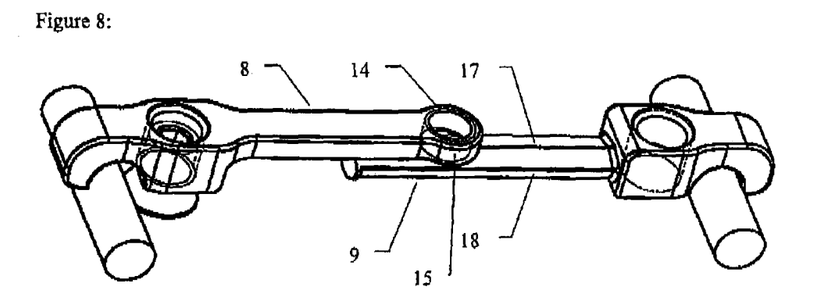
FIG. 8 is a top plan view of the disassembled connected system of FIG. 6 minus the locking screws.

Referring now to FIGS. 6-11, the distal end 28b of the first member 28 is formed with an upwardly facing serrated surface 34 substantially surrounding a threaded locking screw bore 36 as is shown in FIG. 8. A middle coupler 40, in the form of a ring, includes an upper section 40a which is mounted on the distal end of the first member in the assembled condition with a cylindrical opening 40b aligned, i.e., in registration with, but having a slightly larger diameter $d_2$ than the diameter of the head of a coupler locking screw 42 to be described. See FIGS. 10 and 11.

Figures 10, 11:
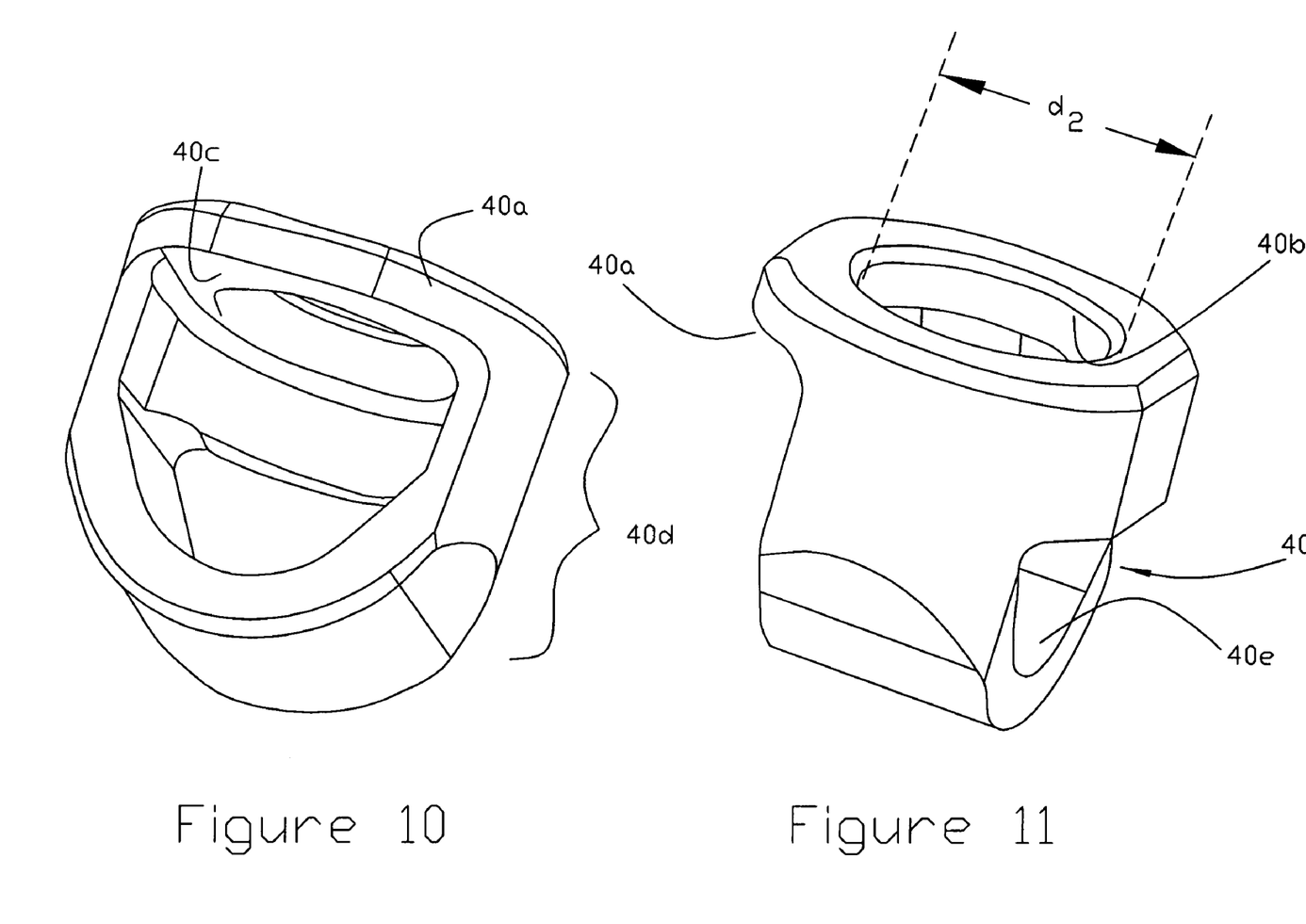
FIGS. 10 and 11 are different perspective views of the coupler of the system of FIG. 6.

A downwardly facing annular flat surface 40c of the coupler is arranged to engage the upwardly facing serrated surface 34 at the distal end of the first member when the system is in its locked position as will be explained in more detail. The serrated surface 34 tends to bite into the coupler surface 40c to inhibit any relative rotation between the coupler and first member in the locked position. In the unlocked position the coupler is free to rotate through a limited angle, e.g., +/−30°, relative to the distal end of the first member.

Figure 9:
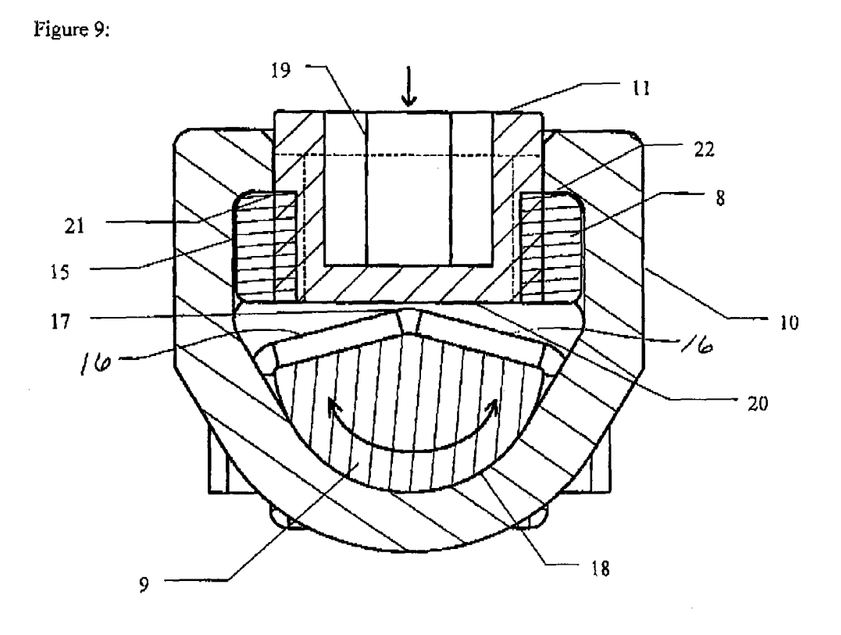
FIG. 9 is a side elevation assembled view of a modified connector system showing an alternative placement of a rod receiving groove in one of the members and also showing a spinal rod captured in that groove.

Instead of locating the rod receiving grooves on the interior side of the elongated members 48 and 28 as shown in FIGS. 7 and 8, one or both of the grooves may be located on the exterior side of the elongated member, i.e., near the distal end or remote from the coupler as is indicated at 14' in FIG. 9. This arrangement would allow the rod receiving grooves to slide as closely together as dimensionally allowed while preserving the ability of the system to accommodate various spatial orientations of the spinal rods.

The coupler is mounted on the distal end of the first member by means of a locking member such as a locking set screw 42, preferably having an enlarged head 42a seated within the opening 36. The set screw has a threaded shaft 42b which is received in the locking screw opening 36. See FIGS. 12 and 13. A generally u-shaped lower section 40d of the coupler terminates in a partial cylindrical or saddle-shaped (i.e., radiused) interior surface 40e and defines an opening 46 for cooperating with the bottom surface of the distal end of the first member. The distal end 48b of the second elongated member 48 extends through this opening in the assembled condition.

The distal end 48b of the second member may have a cylindrical cross section, but preferably the distal end 48b has a cross section in the form of a lower rounded surface 48c (matching the curved surface 40e) with two substantially straight sides 48d terminating in a rounded or radiused crown 48e. The crown 48e preferably has a radius $r_1$ concentric to the radius of the surface 40e. The latter configuration allows for a reduced height profile while preserving the bending stiffness in the plane of the spinal rods.

In the assembled condition, before the locking screw is tightened, the second elongated member is free to move longitudinally and/or rotate about its axis $X_3$ relative to the first member. See FIGS. 6, 9, 12 and 13. The second member is also free to pivot through a limited angle about an axis Y perpendicular to the longitudinal axis $X_1$, via the coupler. See FIG. 6. The three degrees of freedom facilitate the surgeon's ability to accommodate normal spatial orientations of the spinal rods.

Figure 12:
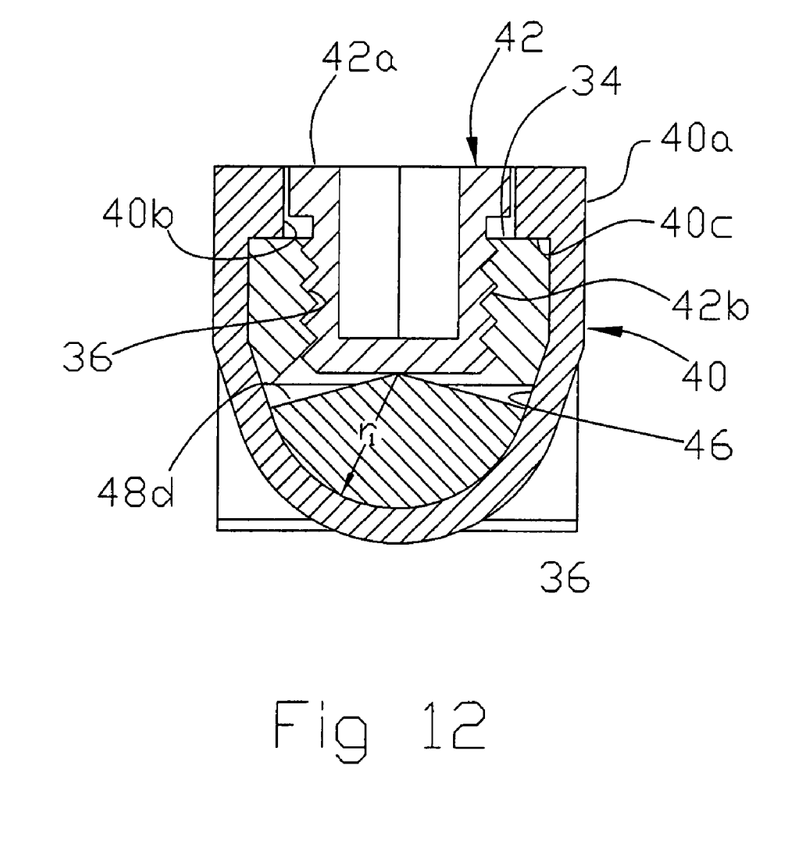
FIGS. 12 and 13 are cross-sectional views taken along line 11-11 of FIG. 9 demonstrating the rotation of the second member about its longitudinal axis relative to the first member.
Figure 13:
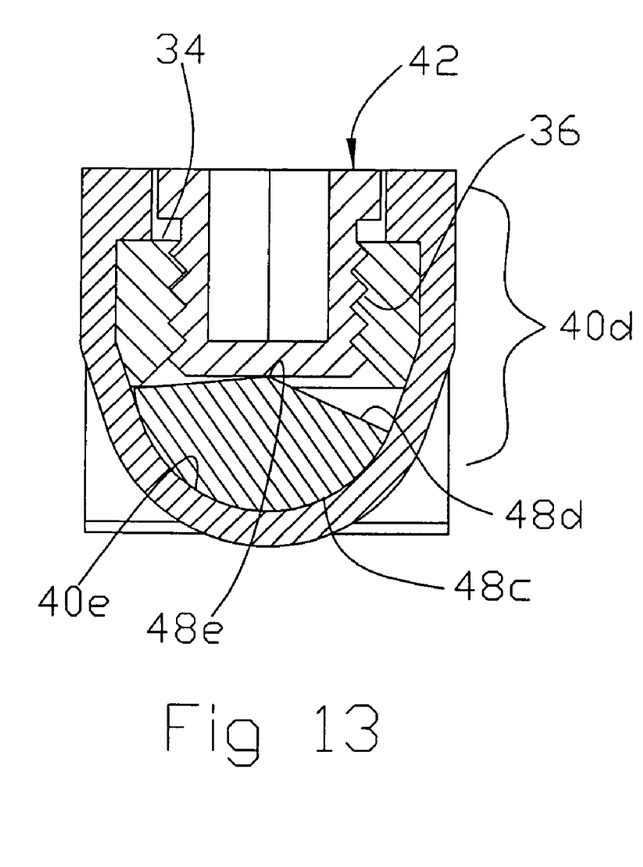

During installation the rod receiving grooves of the system may be positioned angularly with respect to each other and moved towards or away from each other. Once the clamping set screws are retracted to lock the assembly to the rods, the connector assembly may then be locked in a fixed position by advancing the locking set screw to force the portion of the distal end of the second member within the coupler downwardly to clamp it between the end of the set screw and the coupler internal surface 40e. This action also forces the distal end of the first member upwardly to lock the surfaces 40c and 34 together as is illustrated in FIGS. 12 and 13.

The component parts of the connector system may be made of any high strength materials, such as medical grade steel or titanium compound, suitable for implantation into the human body.

By way of example, the first and second elongated members may have a length and width of about 1" and ¼", respectively.

Figure 14:
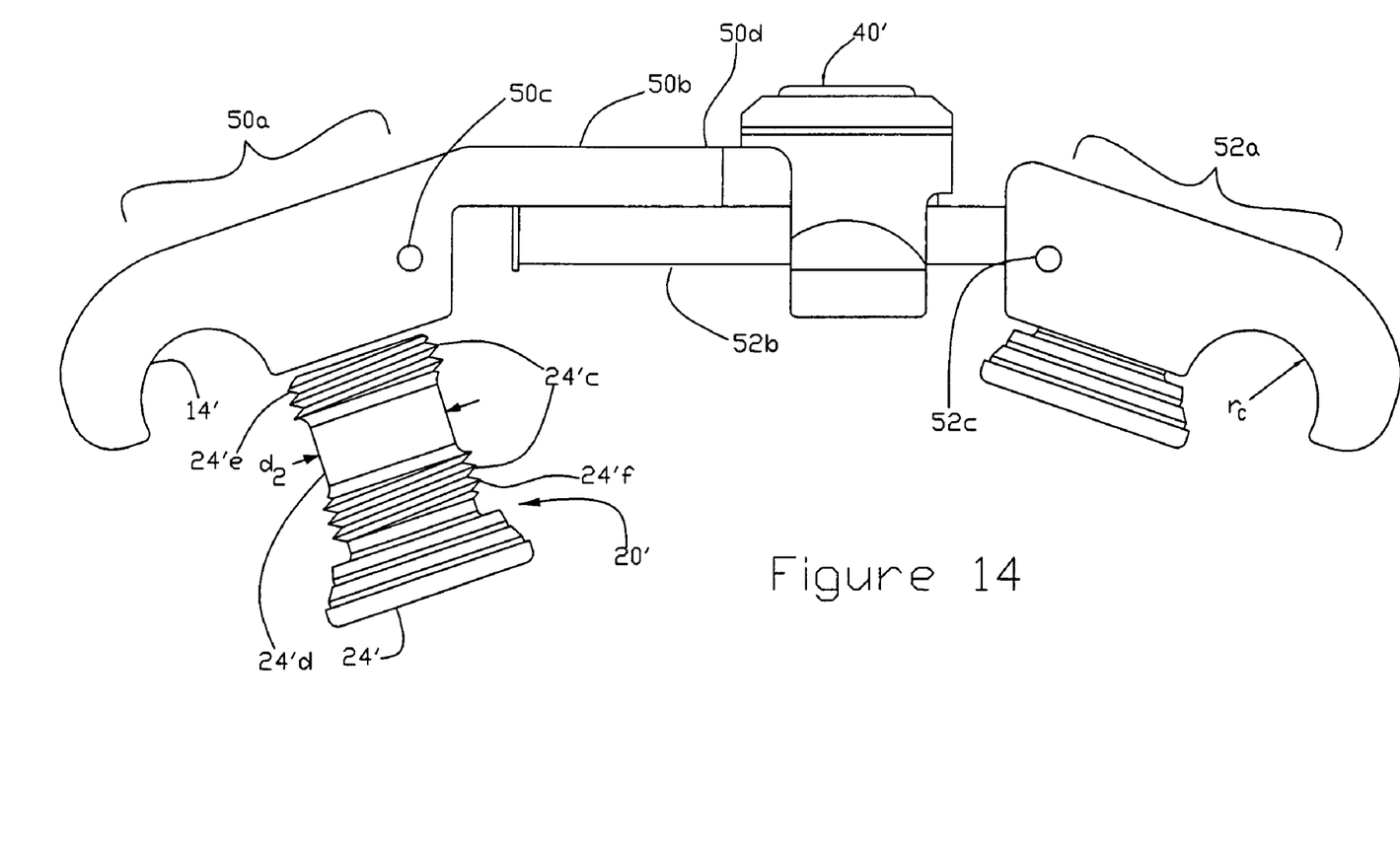
FIG. 14 is a side elevation view of a modified universal connector system like the system of FIG. 9, with the proximal ends of the elongated members canted at an angle to the longitudinal axis to accommodate the natural lateral curvature of the vertebrae.
Figure 15:
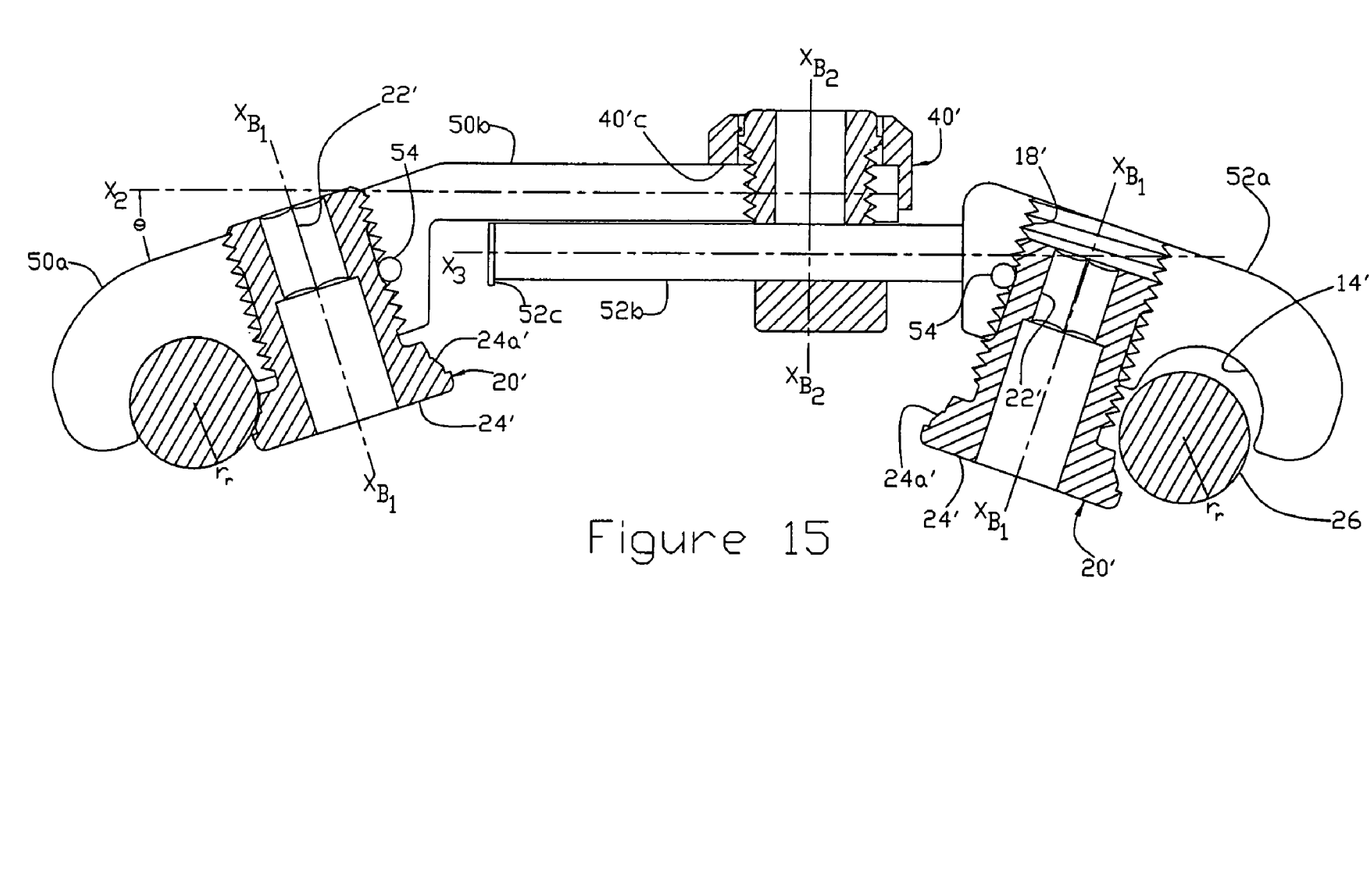
FIG. 15 is a cross-sectional view of the connector system of FIG. 14 showing a spinal rod just entering the rod receiving recess (left side) and fully inserted into the pin receiving bore to clamp a spinal rod in the recess (right side)
Figure 16:
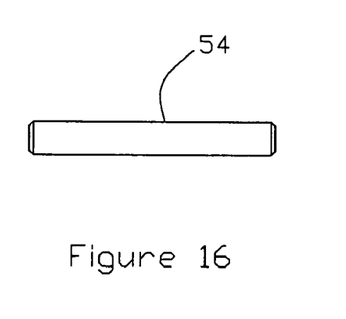
FIG. 16 is a side elevation view of a dowel or pin which may be used to retain the set screw within the proximal end of the elongated members.
Figure 17:
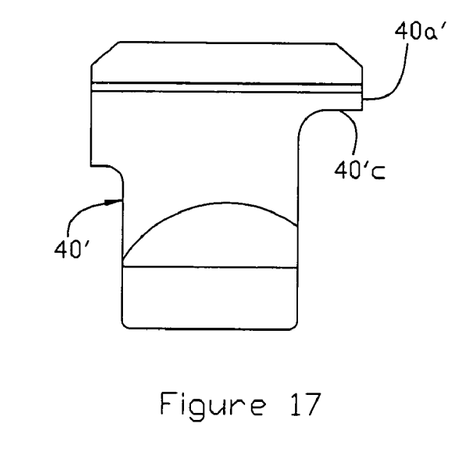
FIGS. 17 and 18 are side elevation and top plan views of a modified locking coupler, respectively.
Figure 18:
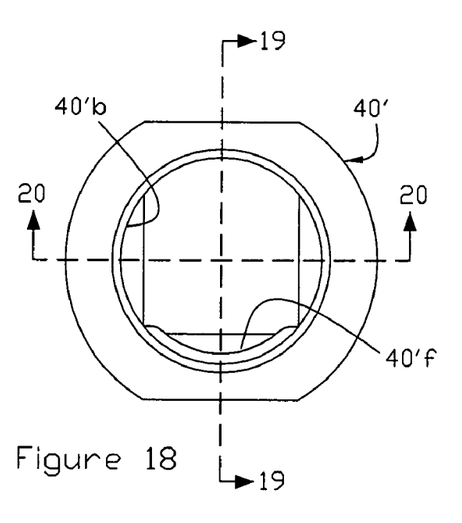
Figure 19:
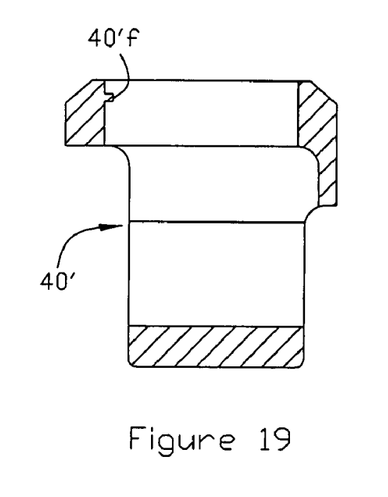
FIGS. 19 and 20 are cross-sectional views of the modified coupler taken along lines 19-19 and 20-20, respectively of FIG. 18.
Figure 20:
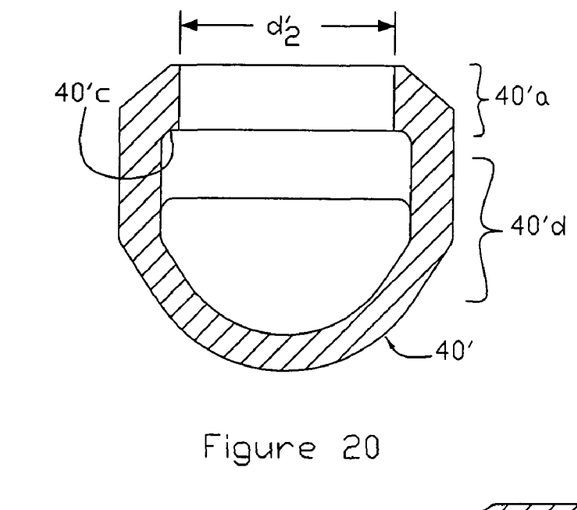
Figure 21:
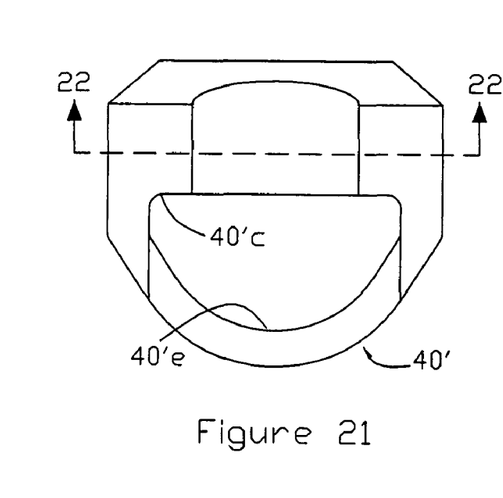
FIG. 21 is a front elevation view of the coupler.
Figure 22:
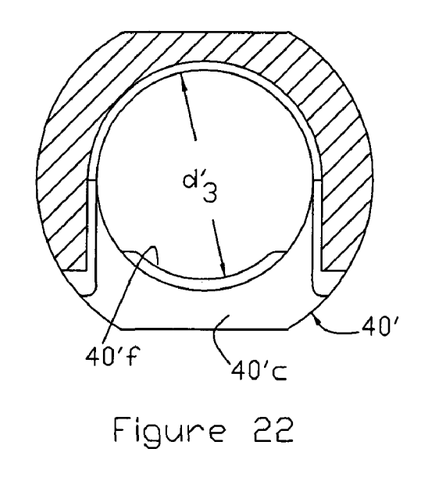
FIG. 22 is a cross-sectional view of the modified locking coupler taken along lines 22-22 of FIG. 21.

Referring now to FIG. 14, a modified transverse connector is comprised of first and second elongated members 50 and 52, respectively, joined via a modified coupler 40'. The distal ends 50b and 52b of the members are aligned along axis X2 and X3 while the proximal ends 50a and 52a are offset at an acute angle, say within a range of about 10° to 25° and preferably about 18° from the respective longitudinal axii as shown more particularly in FIG. 15 to allow the connector, when installed, to accommodate the natural lateral curvature of the underlying vertebrae. The proximal ends of each elongated member define a spinal rod receiving recess 14' which extends through an arc in excess of 180°, e.g., about 200°, and is formed with a radius $r_c$ which may be slightly smaller than the radius $r_r$ of the spinal rod 26. This configuration allows the rod, when forced into the recess, to slightly deform the material forming the arc and results in a firmly clamped rod within the recess. A clamping set screw receiving bore 18' is located adjacent each recess, similar to the arrangement previously described. A modified rod clamping set screw 20', having a hexagonal wrench receiving surface 22, is provided with an enlarged head 24' having a beveled surface 24'a. The clamping set screw shaft is formed with an interrupted or bifurcated threaded portion, 24'c bracketing an unthreaded intermediate section 24'd. The intermediate or central land section 24'd has a diameter $d_2$ which is the same or slightly smaller than the root diameter of the bifurcated threaded portion 24'c with upper and lower branches 24'e and 24'f extending above and below the land section respectively, as shown. The distal ends of the elongated members have lateral bores 50c, 52c therethrough which intersect the threaded bores 18' within the thread depth as is shown more particularly in FIG. 15. A dowel pin 54 (FIG. 16) is inserted into each of the bores 50c and 52c after the clamping set screws 20' have been threaded into the openings 18' so that the dowel pins 54 ride along the lands 24'd. This arrangement functions as a set screw travel limiting means to allow the set screws to be retracted to accommodate the entry of a spinal rod in the recess 14' (FIG. 15, right side) and subsequently to be advanced to force the respective rods into the recesses (FIG. 15, left side). The dowel pin's abutment against the lower thread branch 24'f prevents the set screw from exiting the connector.

A modified locking coupler 40', for locking the distal ends of the members 50 and 52 together, is shown in FIGS. 17-22. Prime numerals designate like sections of the couplers 40 and 40'. The key difference between the two parts is a coupler locking screw travel limiting means in the form of a lip or shoulder 40'f encompassing an arc of about 30° to 50° and preferably about 40°. The lip 40'f extends inwardly from the upper end of the coupler 40' to partially obstruct the opening 40'b providing a clearance distance $d_3$ which is slightly smaller than the diameter of the peripheral rim on a modified coupler locking set screw 42' to be described.

Figure 23:
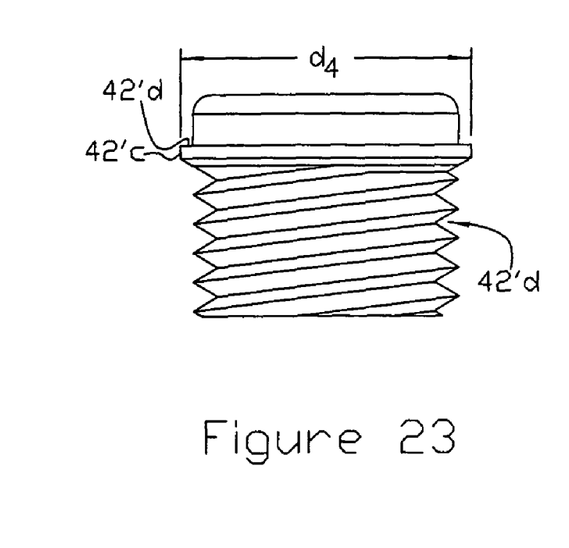
FIGS. 23, 24 and 25 are side elevation, top plan and cross-sectional views respectfully of a modified coupler locking screw.
Figure 24:
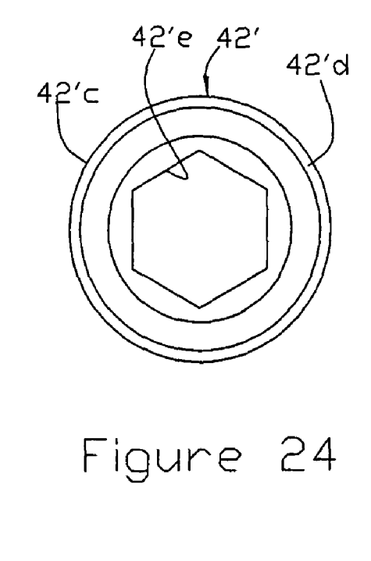
Figure 25:
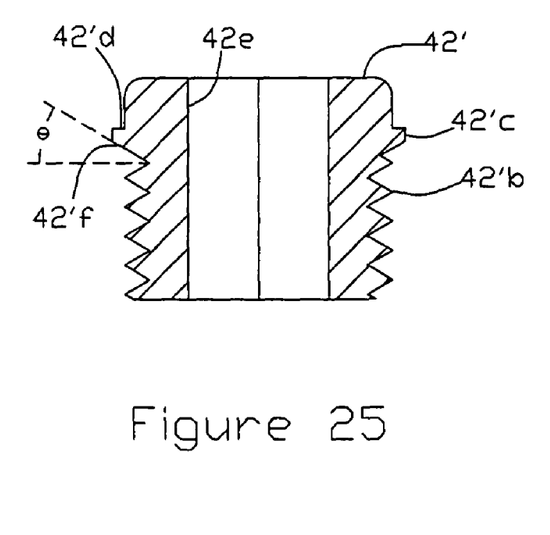

The surface 40'c engages the upper surface 50d (FIG. 14) along the distal end of the elongated member 52 to lock the members 50 and 52 together as has been described in connection with FIGS. 12 and 13. The coupler set screw 42', shown in FIGS. 23-25, is formed with male threaded section 42'b which merges with a upwardly extending section 42'f tapered at an angle φ of about 30° (to the horizontal) to a peripheral rim 40'c having a diameter $d_4$ slightly greater than $d_3$. See FIG. 25. For example, $d_4$ may be 0.2350" while $d_3$ may be 0.230". The rim 40'c defines an upwardly facing annular surface 42'd which is designed to abut the lower surface of the coupler lip 40'f to prevent the set screw 40' from exiting the coupler 40' once the connector system is assembled at the factory. See FIG. 15. The coupler set screw includes a hexagonal wrench engaging surface 42'e. The distal end of the second member 52 is formed with a downwardly protruding flange 52c (FIG. 15) which prevents separation of the elongated members once assembled. During assembly the shoulder 42'c of the coupler set screw is forced beyond the coupler lip 40'f via the tapered section 42'f when the coupler is threaded into the opening in the distal end of the member 52' along axis $X_{B2}$ (FIG. 15). Once assembled the lower surface of the coupler lip 40'g engages the locking screw surface 42'd to prevent the set screw from exiting the connector. The travel limiting means, i.e, the bifurcated clamping set screw threads 24'c, the dowel pins 54, the coupler shoulder 40'f, the locking screw rim 42'd, and the flange 52c maintain the transverse connector of FIG. 15 in its assembled condition. It is to be noted that the same travel limiting means may be incorporated into the transverse connector of FIG. 6.

The transverse connector system described and illustrated provides a minimum disturbance of the area underlying the spinal rods while accommodating the use of a single instrument or wrench extending directly out of the wound site to secure the system to the rods. An additional advantage is achieved by forming the connector in two separate members with a middle coupler and locking screw for locking the elements together in a desired spatial orientation.

Various modifications of the invention will occur to those skilled in the art without involving any departure from the spirit and scope of the invention as called for in the appended claims.

What is claimed is:

1. A transverse connector system for rigidly joining together two spinal rods at a desired spatial orientation comprising:

a connector formed of first and second elongated members, a middle coupler and a locking member, each elongated member defining a longitudinal axis, proximal and distal ends, and having a rod receiving recess and a receiving bore adjacent each rod receiving recess, each rod receiving recess and receiving bore being located on a proximal end of each elongated member, the middle coupler being mounted on the distal end of the first elongated member for enabling limited pivotal movement about an axis substantially perpendicular to the longitudinal axis of the first elongated member, the distal end of the second elongated member is configured for extending into the middle coupler for relative movement along and rotation about its longitudinal axis, the locking member being arranged to lock the distal ends of the first and second elongated members together at a desired relative rotational alignment, and a clamping pin member is disposed within each receiving bore, the clamping pins are arranged to be retracted within their associated bores to capture the spinal rods within the rod receiving recesses and rigidly join the rods to the connector, and the distal end of the first elongated member defines a threaded cylindrical locking member receiving bore, and the middle coupler has a U-shaped lateral side opening extending through the middle coupler with an upper section defining an opening in registration with the first elongated member and a lower section defining a radiused interior surface through which the distal end of the second member extends and wherein the locking member is in the form of a coupler set screw threadably received in the threaded cylindrical bore in the distal end of the first elongated member whereby advancement of the coupler set screw locks the distal ends of the first and second elongated members together at the desired relative rotational and longitudinal alignment.

2. The transverse connector system of claim 1 wherein the distal end of the first elongated member defines an upwardly facing serrated surface extending around the threaded locking member receiving bore therein and wherein the middle coupler defines a downwardly facing surface surrounding the opening therein whereby advancement of the coupler set screw forces the distal end of the second elongated member against the radiused interior surface and the serrated distal end of the first elongated member against the downwardly facing surface of the coupler to lock the distal ends of the elongated members together.

3. The transverse connector system of claim 1 wherein the first elongated member includes a solid flat sided cross sectional rectangular configuration provided between the proximal end to the distal end.

4. The transverse connector system of claim 1 wherein the second elongated member includes a solid curved rotational surface on a first surface and a pair of flat surfaces, each extending respectively from the curved rotational surface to an intersection crown of the respective flat surfaces between the proximal to the distal ends.

5. The transverse connector system of claim 4 wherein the coupler is configured to enable three degrees of movement between the first and second elongated members to be provided and a desired spatial orientation to be fixed.

6. A spinal rod connector system for connecting together spinal rods at a desired spatial orientation comprising:
   a first elongated member having a rod receiving recess at a first proximal end, a threaded bore, at a first distal end, extending through the first elongated member, and a first intermediate bridging portion extending between the first proximal and the first distal end with at least one flat surface extending substantially traverse to and parallel to a longitudinal axis of the first intermediate bridging portion;
   a second elongated member having a rod receiving recess at a proximal end and second distal end, and a second intermediate bridging portion extending between the second proximal end and the second distal end with a curved rotational surface on a first side of the second intermediate bridging portion and a pair of flat surfaces, each extending respectively from the curved rotational surface to an intersection crown of the respective flat surfaces that extends parallel to a longitudinal axis of the second intermediate bridging portion;
   a locking set screw; and
   a coupler having a first opening to receive the locking set screw and a second elongated member opening of an approximately U-shaped section configured to mount the distal end of the first elongated member adjacent the first opening to enable alignment of the threaded bore with the first opening, an interior surface of the U-shaped section is configured to rotably receive the distal end and curved rotational surface, wherein the flat surface and intersecting crown can be aligned and fixed by both the locking set screw and contact with the flat surface when extended through the threaded bore to fix a relative rotable position of the first and second elongated members.

7. A spinal rod connector system of claim 6 wherein the first elongated member has a serrated surface adjacent the threaded bore.

8. The transverse connector system of claim 6 wherein the coupler is configured to enable three degrees of movement between the first and second elongated members to be provided and a desired spatial orientation to be fixed.

9. A variable transverse connector system for joining together first and second spinal rods, comprising: a first elongated member having a first longitudinal axis with a first proximal end having a first set locking receiving bore and a first distal end, the first elongated member having a first intermediate bridging portion extending between the first proximal end and the first distal end with at least one flat surface extending substantially traverse to and along the longitudinal axis; a locking member configured for fastening the first distal end;
   a second elongated member having a second longitudinal axis with a second proximal end having a second set locking receiving bore and a second distal end, the second elongated member having a second intermediate bridging portion, extending between the second proximal end and the second distal end, with a curved rotational surface on a first side of the second elongated member and a pair of flat surfaces, each extending respectively from the curved rotational surface to meet at an intersection crown of the respective flat surfaces, along and parallel to the second longitudinal axis, on a second side of the second elongated member;
   a first set locking member configured to engage the first set locking receiving bore;
   a second set locking member configured to engage the second set locking receiving bore;
   a first spinal rod receiving surface member wherein the first set locking member can lock an adjacent first spinal rod on the first spinal rod receiving surface member;
   a second spinal rod receiving surface member wherein the second set locking member can lock an adjacent second spinal rod in the second spinal rod receiving surface member; and
   a coupler member having a substantially U-shaped opening with a lower rotational surface complementary in shape to receive and enable rotation of the curved rotational surface of the second elongated member with an upper portion of the U-shaped opening engaging the first elongated member with the flat surface aligned to enable rotation about the longitudinal axis and relative movement of the pair of flat surfaces of the second elongated member in and through the coupler U-shaped opening wherein an adjustment of the relative alignment between the first and second elongated members can be accomplished and the locking member can lock the first and second elongated members together within the U-shaped opening in a desired spatial orientation.

10. The variable transverse connector system of claim 9 wherein the first elongated member includes a solid cross sectional rectangular configuration between the first proximal end and the first distal end.

11. The variable transverse connector system of claim 9 wherein the coupler member is configured to enable three degrees of movement between the first and second elongated members to be provided and a desired spatial orientation to be fixed.

12. A variable transverse connector system for joining together first and second spinal rods, comprising: a first elongated member having a first longitudinal axis with a first proximal end having a first set locking receiving bore and a first distal end, the first elongated member having a first intermediate bridging portion extending between the first proximal end and the first distal end with at least one flat surface extending substantially traverse to and along the longitudinal axis; a locking member configured for fastening the first distal end;
   a second elongated member having a second longitudinal axis with a second proximal end having a second set locking receiving bore and a second distal end, the second elongated member having a second intermediate bridging portion, extending between the second proximal end and the second distal end, with a curved rotational surface on a first side of the second elongated member and a pair of flat surfaces, each extending respectively from the curved rotational surface to meet at an intersection crown of the respective flat surfaces, along and parallel to the second longitudinal axis, on a second side of the second elongated member;

a first set locking assembly configured to engage the first set locking receiving bore with an engaging surface portion axially offset from an axis of the first set locking receiving bore;

a second set locking assembly configured to engage the second set locking receiving bore with an engaging surface portion axially offset from an axis of the second set locking receiving bore;

a first spinal rod receiving surface member wherein the first set locking assembly can lock an adjacent first spinal rod on the first spinal rod receiving surface member with an adjustment of the engaging surface portion to contact the first spinal rod;

a second spinal rod receiving surface member wherein the second set locking member can lock an adjacent second spinal rod in the second spinal rod receiving surface member with an adjustment of the engaging surface portion to contact the second spinal rod; and a coupler member having a substantially U-shaped opening with a lower rotational surface complementary in shape to receive and enable rotation of the curved rotational surface of the second elongated member with an upper portion of the U-shaped opening engaging the first elongated member with the flat surface aligned to enable rotation about the longitudinal axis and relative movement of the pair of flat surfaces of the second elongated member in and through the coupler U-shaped opening wherein an adjustment of the relative alignment between the first and second elongated members can be accomplished and the locking member can lock the first and second elongated members together within the U-shaped opening in a desired spatial orientation at any position substantially extending between an extension of the first and second intermediate bridging portion so that the first and second distal portions are fastened together to an overlapping of the first and second intermediate bridging portions and the coupler member is adjacent the second proximal end.

13. The variable transverse connector system of claim 12 wherein the first elongated member includes a solid cross sectional rectangular configuration between the first proximal end and the first distal end.

14. The variable transverse connector system of claim 13 wherein the coupler member is configured to enable three degrees of movement between the first and second elongated members to be provided and a desired spatial orientation to be fixed.

* * * * *